United States Patent [19]

Ehrlich et al.

[11] Patent Number: 5,250,026
[45] Date of Patent: Oct. 5, 1993

[54] ADJUSTABLE PRECISION TRANSPONDER INJECTOR

[75] Inventors: Paul Ehrlich, Loveland; Larry J. Dixon, Lakewood; Robert C. Stewart, Littleton, all of Colo.

[73] Assignee: Destron/IDI, Inc., Boulder, Colo.

[21] Appl. No.: 889,535

[22] Filed: May 27, 1992

[51] Int. Cl.$^5$ .............................................. A61D 7/00
[52] U.S. Cl. ........................................ 604/60; 604/117
[58] Field of Search ............................ 604/57, 59–64, 604/117, 240, 241, 243; 606/116, 117

[56] References Cited

U.S. PATENT DOCUMENTS

| 1,601,932 | 10/1926 | Viol | 604/64 |
| 2,569,901 | 10/1951 | Richard | 604/117 |
| 3,483,810 | 12/1969 | Peters et al. | 604/117 |
| 3,538,916 | 11/1970 | Wiles | 604/117 |
| 3,744,493 | 7/1973 | Boober et al. | |
| 4,105,030 | 8/1978 | Kercso | 604/63 |
| 4,231,368 | 11/1980 | Becker | 604/117 |
| 4,373,526 | 2/1983 | Kling | 604/117 |
| 4,820,267 | 4/1989 | Harman | 604/60 |
| 4,841,985 | 6/1989 | Wanamaker | 604/240 |
| 4,936,827 | 6/1990 | Grimm et al. | 604/240 |
| 5,002,548 | 3/1991 | Campbell et al. | 606/116 |

FOREIGN PATENT DOCUMENTS 2021303 3/1991 Canada .

Primary Examiner—Ralph Lewis
Attorney, Agent, or Firm—Homer L. Knearl

[57] ABSTRACT

An implant injector for animals is adjustable for implant insertion depth. The distance, that the injector needle or cannula, extends past the nose of the injector is adjustable. The insertion depth adjustment is accomplished by moving the nose of the injector relative to the tip of the cannula that extends past the nose. In addition to adjusting the insertion depth, the cannula or needle, may also be rotated to a plurality of positions relative to the injector handle.

A spring loaded plunger, when released by a release button, will push the implant out the end of the cannula as the operator withdraws the cannula from the animal. The release button is designed as a safety trigger to avoid premature activation of the plunger during insertion of the needle.

Needles, or cannulas of various diameters and lengths, may be interchanged in the injector. Also, the spring loaded plunger for expelling the implant may be removed allowing the operator to replace the plunger with a different diameter and length plunger, if desired, to match different size cannulas.

10 Claims, 4 Drawing Sheets

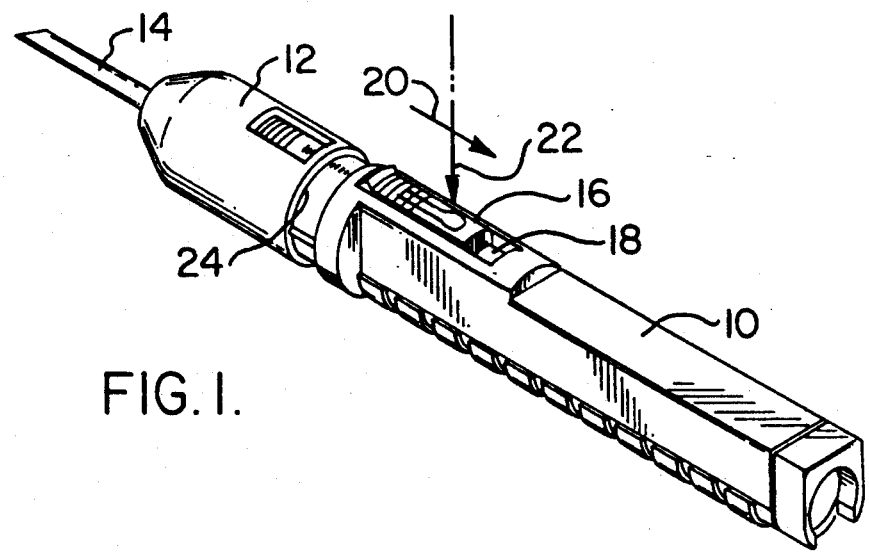
FIG. 1.
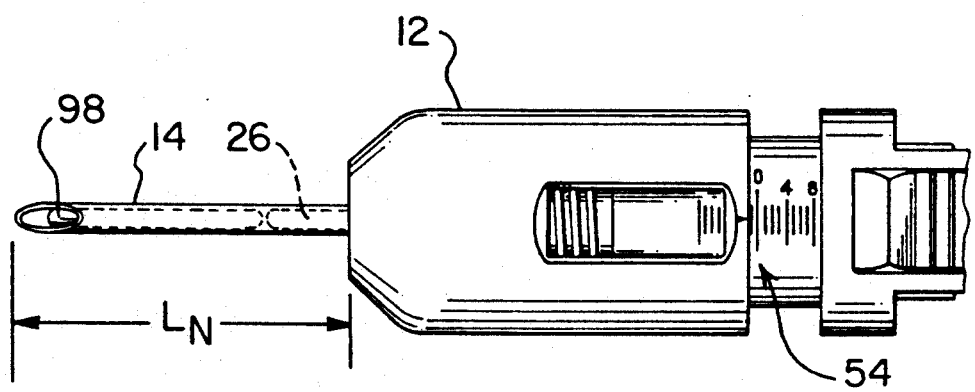
FIG. 3.
|  | SMALL | MEDIUM | LARGE |
|---|---|---|---|
| NEEDLE LENGTH | 55.88 | 64.77 | 77.98 |
| NEEDLE INSIDE DIAM. | 2.39 | 3.43 | 3.81 |
| NEEDLE OUTSIDE DIAM. | 3.05 | 4.19 | 4.57 |
| TRANSPONDER DIAM. | 2.08 | 3.00 | 3.50 |
| NOMINAL INSERTION | 38.86 | 47.75 | 55.88 |
DIMENSIONS IN MILLIMETERS
FIG. 4.

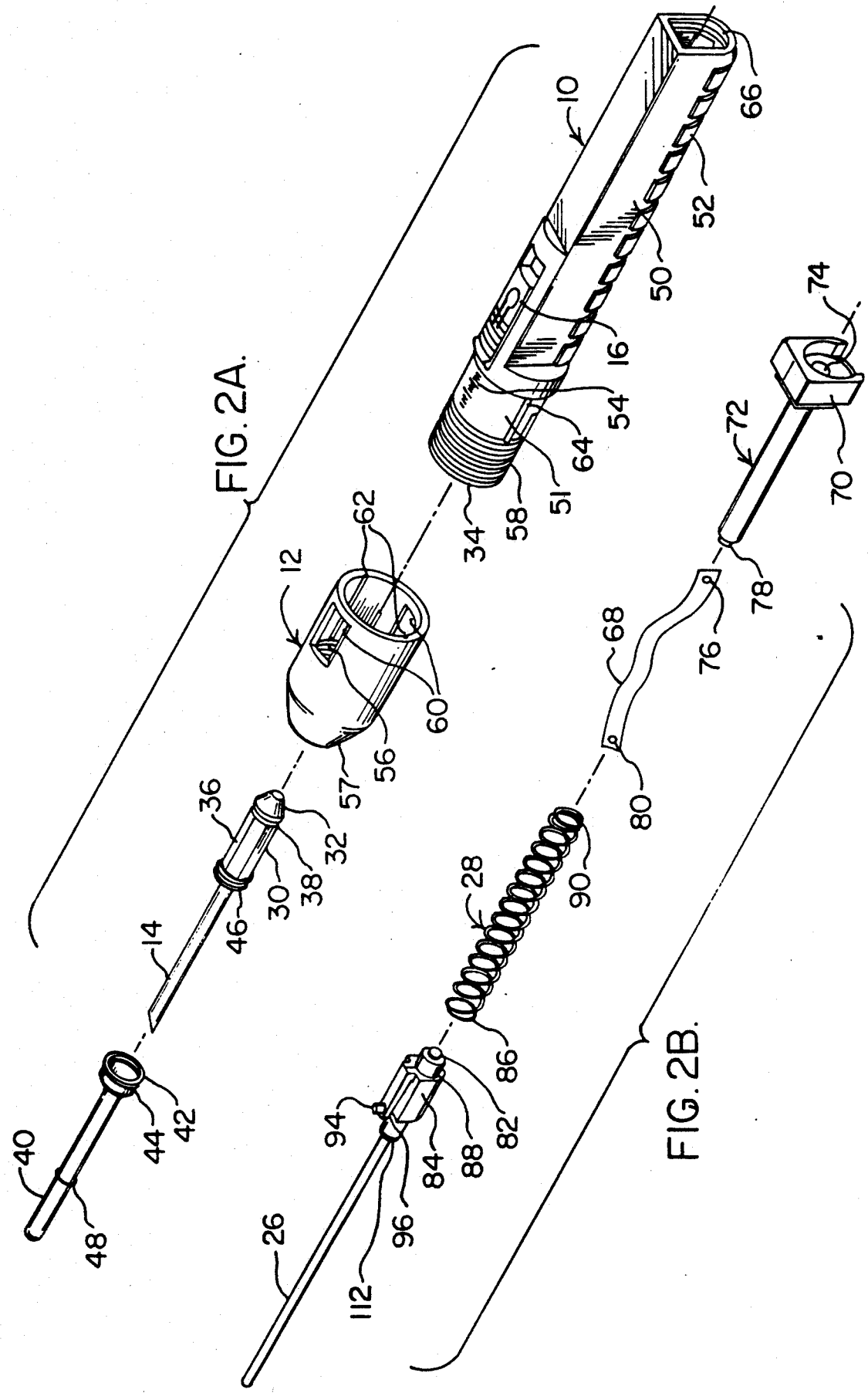

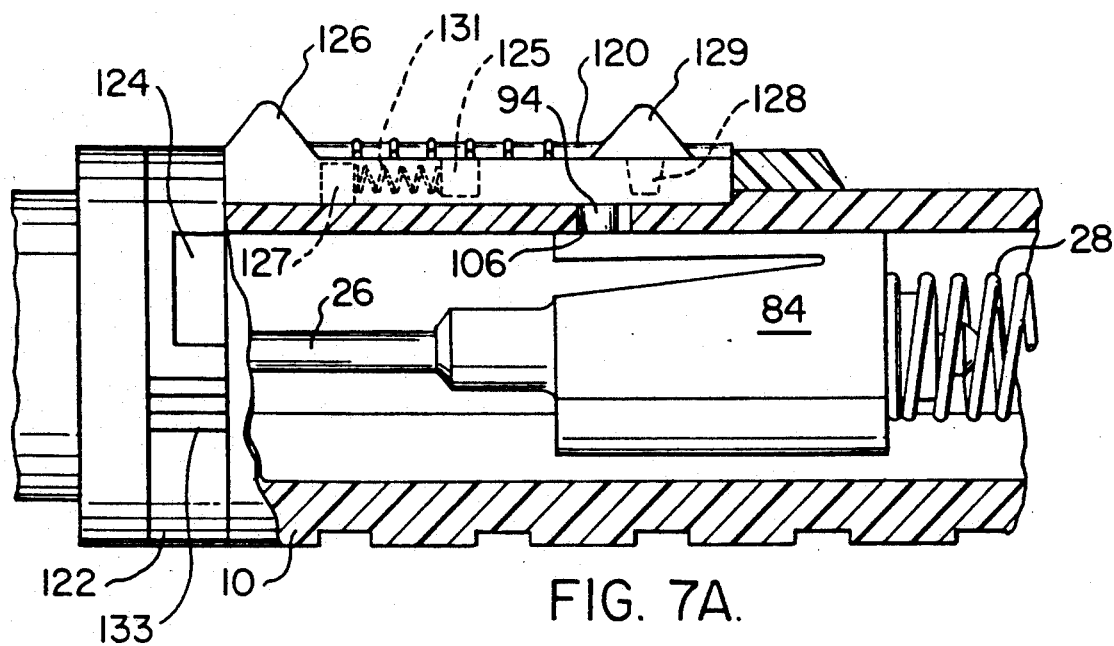
FIG. 7A.
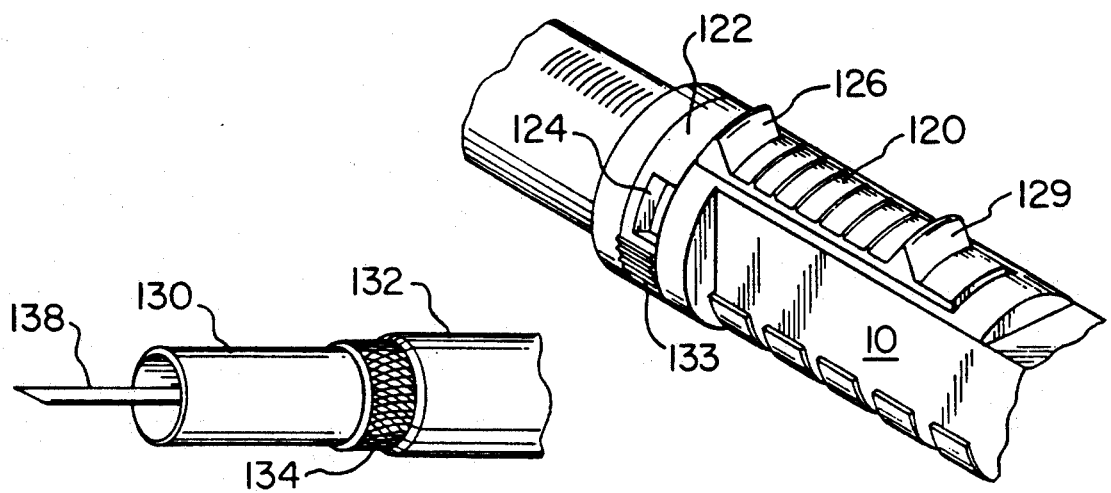
FIG. 8B.
FIG. 7B.
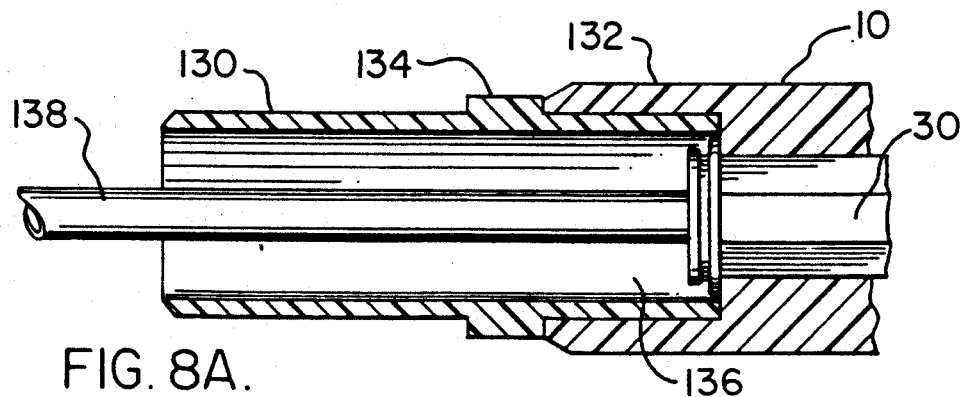
FIG. 8A.

ADJUSTABLE PRECISION TRANSPONDER INJECTOR

BACKGROUND OF THE INVENTION

1. Field of the Invention

This invention is directed to a method and apparatus for injecting implants subcutaneously in animals. More particularly, the invention relates to injecting implants, such as identification transponders, to precisely controlled distances from the point of injection. Furthermore, the injector is adjustable to be able to inject animals that range in size from small laboratory animals such as mice to large farm livestock such as cattle.

2. Description of Prior Art

Transponder, or pellet implanters, are well known. However, they have been designed for specific tasks with little or no adaptability for injection to different depths in a large variety of animals.

An early example of a pellet implanter is U.S. Pat. No. 3,744,493, issued to Boober et al. Boober et al used a simple pellet implanter having a manual plunger to force the pellets out of the end of the needle. Another simple implanter is U.S. Pat. No. 4,820,267, issued to S. M. Harmon. Harmon used a retractable cannula, or needle, and fixed plunger to force the pellets out the end of the needle when the needle is retracted. The needle is removable to load the next pellet cartridge. Also, the needle may be marked so the operator can tell the depth of implant by inserting the needle to the mark. However, holding a needle at a particular mark on the needle while injecting an animal is not practical. Unless the animal is anesthetized, it will react to the needle sting and will move during implanting. Thus, it is very difficult to hold the needle at a given insertion depth based on a mark on the needle.

One attempt to deal with the problem of controlling the depth of implant is shown in the Canadian Patent Application 2,021,303 by H. de Jong published Mar. 1, 1991. De Jong uses a transponder implanter with a touch-release button for releasing a plunger to push the transponder out of the needle as the implanter is removed from the animal. The touch-release button is at the front of the implanter at the base of the needle. Accordingly, the length that the needle extends past the touch release button controls the depth of the implant. The difficulty with de Jong's implanter is that once it is cocked and ready to fire, it is very unstable. Any contact with the touch-release button will expel the transponder from the implanter. In addition, if the animal moves while the injector is in the animal, a bump to the touch-release button will cause premature triggering of the injector while the needle is in a wrong position. Furthermore, de Jong has no way to adjust the depth of the implant.

The prior art does not solve the problem of injecting implants to a predetermined adjustable depth. Further, all of the injectors are designed to deal with animals of a particular size. The injectors are not adjustable so as to be able to inject implants in animals that vary over a wide range of sizes from farm livestock to laboratory test animals.

SUMMARY OF THE INVENTION

It is an object of this invention to adjust the cannula, or needle length extension, from the front of the implant injector, and thereby control the depth of the implant.

It is an object of this invention to provide a controlled release of the implant when the needle is at the desired subcutaneous depth.

It is a further object of this invention to adjust the orientation of the needle relative to the injector handle.

It is a further object of this invention to provide an implant injector that may be used with both large and small animals.

In accordance with this invention, the above objects are accomplished by an adjustable depth, implant injector having a handle with a implant release button activated by the operator when the injector needle is at the proper insertion depth. The insertion depth, i.e., the length that the injector needle, or cannula, extends past the nose of the injector is adjustable. The nose of the injector acts as a stop surface to control the insertion depth of the needle. The insertion depth adjustment is accomplished by moving the nose of the injector relative to the tip of the cannula. In the preferred embodiment, the nose is threaded on the front of the injector and may be rotated to change the stop surface position. In an alternative embodiment, the stop surface is adjusted by exchanging the nose of the injector with a nose of a different length.

In operation, the position of the insertion stop is adjusted by the operator, the needle or cannula is inserted under the skin of the animal until the stop contacts the animal. When the operator is sure that the depth is correct, he presses the release button for the implant. A spring-loaded plunger, when released by the release button, pushes forward inside the cannula, and loads the implant in the cannula with a force that will push the implant out the end of the cannula as the operator withdraws the cannula from the animal.

The release button is designed as a safety trigger to avoid premature activation of the plunger during insertion of the needle. In one design, the release button must be moved opposite to the insertion direction of motion before it is operative. In a second design, the release button moves the same direction as the insertion motion to become operative, but a trigger release must be moved before the release button can be moved to the operative position.

In addition to adjusting the extension of the needle, or cannula, past the stop surface, the cannula needle may also be rotated to a plurality of positions (45° increments are shown) relative to the injector handle. The cannula has a base with facets that mate with similar shaped cavity at the front of the injector. A quick release is provided between the cannula base and the injector so that the cannula may be removed, rotated and reinserted at one of the available rotary positions. Since the cannula front edge has a cross-sectional bevel cut, this allows the operator to adjust the angle of the bevel cut relative to the implant handle for optimum position in inserting the cannula under the skin of the animal.

Further, needles, or cannulas of various diameters and lengths, may be interchanged in the injector. The length of the cannula is predefined to a nominal dimension coordinated with the stop surface of the injector. A small animal needle will have a smaller diameter and shorter length than a large animal needle. In both cases, the needles will have a predefined length coordinated with nominal insertion depth for the injector. After mounting the needle in the injector, the operator may then adjust the insertion depth plus or minus from the nominal depth by moving the adjustment mechanism of the injector, or by changing the nose of the injector.

The entire injector can be disassembled by hand to interchange parts or for cleaning. The needles, or cannulas, use a common base for interchangeable mounting in the injector. The injector has a pushbutton release for the cannulas whereby they may be quickly removed and replaced. Also, the springloaded plunger for expelling the implant may be removed from the injector without the use of tools. This allows the operator to replace the plunger with a different diameter and length plunger, if desired, to match different size cannulas.

Other objects, advantages and features of the invention will be understood by those of ordinary skill in the art after referring to the complete written description of the preferred embodiments in conjunction with the following drawings.

BRIEF DESCRIPTION OF THE DRAWINGS

FIG. 1 shows the injector of the present invention.

FIGS. 2A and 2B are an exploded view of the injector in FIG. 1.

FIG. 3 illustrates the injector loaded with an implant and ready for use in injecting the implant subcutaneously in an animal.

FIG. 4 is a table of dimensions of typical embodiments of the invention for use with small, medium and large animals.

FIGS. 7A and 7B illustrate an alternative design for the plunger release mechanism incorporating a safety release.

FIGS. 8A and 8B illustrate an alternative design for the adjustable nose of the injector.

DESCRIPTION OF THE PREFERRED EMBODIMENTS

Figure 5A:
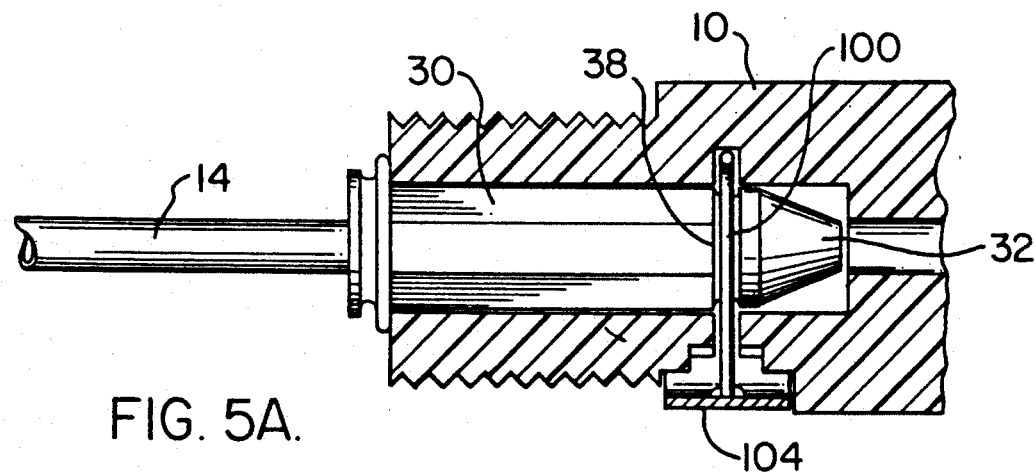
FIGS. 5A, 5B and 5C show the base of the cannula and the cannula release mechanism used in interchanging cannula and indexing the cannula to one of eight angular orientations.

The preferred embodiment of the implant injector, as shown in FIG. 1, incudes a hollow handle 10, an adjustable nose 12, and a hollow needle or cannula 14. Inside handle 10 is a spring-loaded plunger that moves inside cannula 14. When an implant, such as an identification transponder, is inserted in the distal end of cannula 14, the plunger is pushed partially back into the handle, compressing the plunger spring, until the plunger mechanism is caught by button 16. Release button 16 holds the plunger mechanism until the operator slides the button rearward in slot 18, as indicated by arrow 20, and pushes down on the button, as indicated by arrow 22. This two-step motion will release the plunger so that it will apply a force tending to push the implant out the distal end of the cannula.

Handle nose 12 is hollow and threaded on the inside to engage threads at the forward end of handle 10. Accordingly, the operator rotates nose 12 to adjust the exposed length of needle 14. As will be described hereinafter with reference to FIGS. 2 and 4, rearward edge 24 of nose 12 indicates via a scale embossed on handle 10 the variations in implant depth from a nominal predefined depth.

The structure of the injector is more clearly seen in FIG. 2, which is an exploded view of the handle 10, nose 12, needle 14 and plunger 26 with its spring 28. Hollow needle, or cannula, 14 is made from surgical steel and has a plastic molded base 30. Base 30 has a conical face 32 to assist in guiding the needle as it is inserted into the hollow handle 10 at its front face 34. A cylindrical groove 38, behind the conical face 32, is engaged by a spring clip in the handle 10 to hold the needle base in place in the handle.

Base 30 also has eight side faces 36 so that in cross-section the outer perimeter is shaped as an octagon. The insert cavity in handle 10 for needle base 30 has an octagon shaped perimeter to match the needle base shape. As will be described later in FIG. 5, this shape for the base, and the needle base receiving cavity in the handle, allows the needle to be oriented in one of eight rotational positions relative to the handle orientation, with each position separated by 45° from the next adjacent position.

A needle cover 40 fits over the needle 14 to keep the needle clean, and to protect the operator. A ring 42, inside the flared base 44 of the cover, engages ring groove 46 in the needle base. Ring 42 snaps over groove 46 to retain the cover 40 over the needle. Ring 48, on the outside of the cover, is used to retain the cover in a storage position at the back of handle 10, as will be described hereinafter.

Handle subassembly 10 includes the handle main body 50, a nose adjustment section 51, the plunger release button 16, and the needle release button (see FIG. 5). The handle is molded out of elastomeric plastic, such as Santoprene (trademark of Mansanto Corporation), to provide a semi-soft, comfortable and non-slip gripping surface. The handle main body 50 is rectangular in shape except for a semi-cylindrical lower surface 52. The lower surface 52 of the handle is a ribbed gripping surface. The nose adjustment section 51 is threaded to receive nose 12, and has a scale 54 embossed at the top of the handle.

Hollow nose 12 has interior threads 56 that engage threads 58 on the handle when the nose 12 is screwed on the handle. The front face 57 of nose 12 is a conical shape with smooth rounded edges. The front face also has a cylindrical opening (not shown) so that needle base 30 may pass through the nose for insertion into the handle, as described above. Nose 12 also has two windows, or cut-outs, 60. These windows allow the operator to view the portion of scale 54 covered by the nose 12, and also to reach the needle release button, as will be described in FIG. 5. The interior cavity of nose 12 also has two detents 62 180° apart and 90° from the windows. These detents engage ribs 64 (one shown) on the handle to provide a positive detent lock and tactile feedback to the operator that he has rotated the nose one-half revolution, and changed the insertion depth 1 mm (millimeter). Nose 12 is made of the same elastomeric plastic as the handle 10 so the detents 62 snap over ribs 64 as the nose is rotated.

The plunger subassembly, shown in FIG. 2B, is inserted into the injector through opening 66 at the rear of handle 10. The plunger assembly comprises plunger 26, spring 28, restraint strap 68, and molded end cap 70. End cap 70 has molded into it a hollow tube 72 for storing the needle cover 40. When not in use, the needle cover may be inserted in opening 74 in end cap 70. Ring 48, on the needle cover 40, serves to provide a frictional fit inside tube 72 to retain the cover in a stored position in the tube.

The plunger subassembly is assembled by first fastening the perforation 76, in strap 68, over button 78 molded into the end of tube 72. Next, spring 28 is compressed so that perforation 80, in strap 68, may be fastened over button 82 molded into the base 84 of the plunger 26. End 86 of spring 28 fits over cylinder 88 at the base 84 of the plunger. The other end 90 of spring 88 slides over tube 72, and abuts against the inside surface of end cap 70. The plunger assembly may then be inserted inside the handle 10 through opening 66. Restraint strap 68 prevents overextension of spring 28 when the plunger subassembly is removed for cleaning.

The plunger will slide forward until surface 92 of the plunger abuts the base of the back wall of the insert cavity for the base 30 of needle 14. The plunger will then extend into the hollow needle to the distal end of the needle. When an implant is inserted into the end of the needle, the plunger is pushed back. A detent inside handle 10 engages pin 94 to hold the plunger in this loaded position. Pin 94 is mounted on flexible member 96 molded into the base of the plunger. When release button 16 presses down on pin 94, member 96 flexes and pin 94 slips out of its detent, and the plunger moves forward in the needle to push the implant out of the needle as the needle is removed from the animal. The force with which the implant is pushed from the needle can be adjusted by exchanging a spring with a different spring force for spring 28. The release mechanism is described in more detail hereinafter with reference to FIG. 6.

In FIG. 3, the subcutaneous insertion depth $L_N$ is the distance from the front of nose 12 to the end of the needle 14. Shown inside the hollow needle 14 is the implant 98, such as an identification transponder, and the plunger 26. The insertion depth is adjusted by rotating the nose 12. Each half revolution of the nose clockwise extends the insertion depth $L_N$ one millimeter; each half revolution counter clockwise reduces $L_N$ one millimeter. Scale 54 is calibrated in millimeter intervals. Adjustments may be made 8 millimeters either side of a nominal insertion depth indicated by the "0" at the center of scale 54.

The table in FIG. 4 indicates nominal insertion depths in inches for three different preferred embodiments: for small animals, such as rodents; medium sized animals, such as cats, dogs, monkeys; and large animals including livestock such as pigs, cattle, horses. FIG. 4 also indicates preferred dimensions in inches for needle diameters, transponder diameters, and needle lengths. The effective plunger length is changed by placing a collar over the plunger inside the handle to limit the forward movement of the plunger. While the table in FIG. 4 gives the preferred dimensions, the invention may be adapted to a large range of dimensions.

In FIG. 5A, the details of the needle release may be seen. The needle base 30 is held in the handle 10 by spring clip 100. As the base of the needle is inserted into the handle, conical face 32 opens spring clip 100. When the base is completely inserted into the handle, clip 100 snaps into ring groove 38.

Figure 5C:
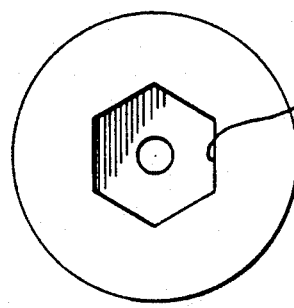
Figure 5B:
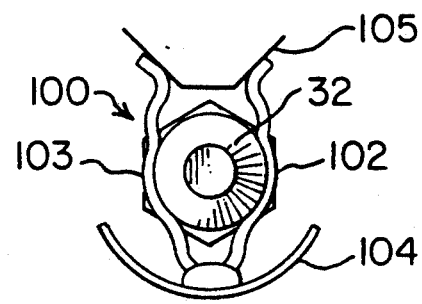

FIG. 5B is a front view of the clip 100. The legs 102 and 103 of the clip spread apart over the conical face 32 of the needle base, and then snap into the ring groove 38 to hold the needle firmly in the handle. To release the needle from the handle, button 104 is pushed upward by the operator, and legs 102 and 103 are spread by cam surface 105 until the the legs are lifted out of ring groove 38. The needle and its base may then be pulled from handle 10.

FIG. 5C is a frontal view of the cavity in the handle that receives the needle base. There are eight walls 108 in the cavity that match the eight facets 36 of the needle base. Accordingly, the needle base may be inserted into the cavity in any one of eight (45°) rotational orientations. This allows the operator to orient the point of the needle in one of eight rotational positions relative the handle. While eight positions are shown for the preferred embodiment, any number of rotational positions and facets on the needle base and handle cavity might be used. For example, 20 positions (and 20 facets) could be used to provide 18° increments in rotational position.

Figure 6:
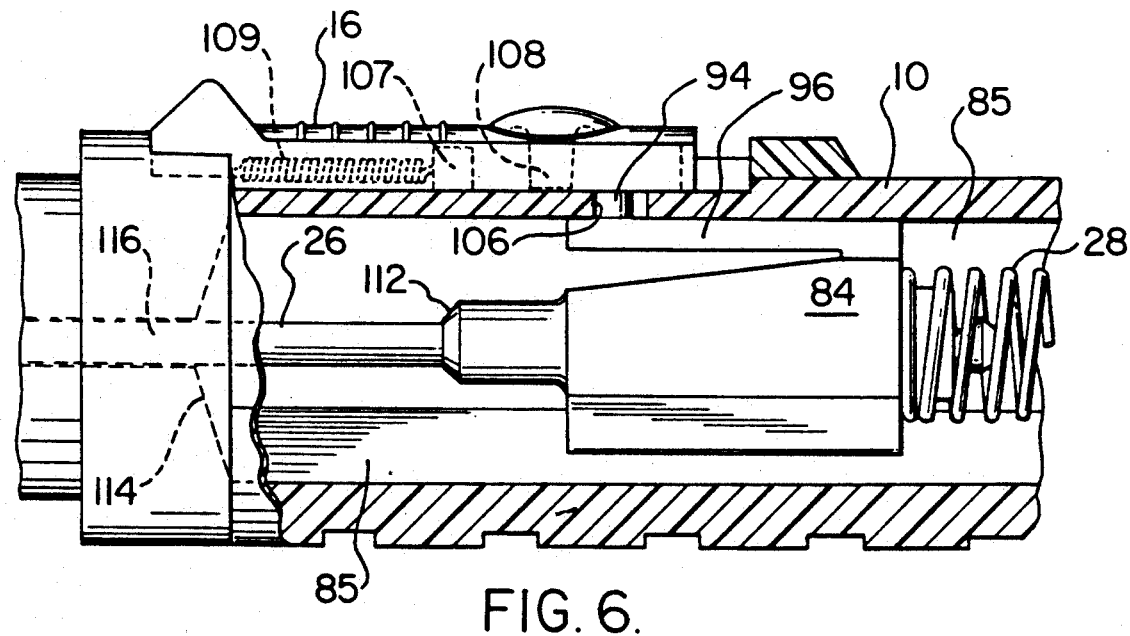
FIG. 6 shows the plunger release mechanism used in the injector of FIG. 1.

FIG. 6 is a cutaway side view of the plunger release button 16 and plunger latch mechanism. The plunger latch comprises pin 94 carried by spring member 96 which is a part of the plunger base 84. Spring member 96 pushes pin 94 upward so that it catches in detent 106 when the plunger is pushed rearward in the handle.

The plunger base 84 has a cross-sectional shape (pentagonal) that matches the cross-sectional shape of the plunger cavity 85 in handle 10. The matched shapes keep the plunger base 84 correctly oriented so that pin 94 is aligned with detent 106. To reduce cost, the plunger base 84 could be molded with ribs rather than solid, as shown in FIG. 6. All that is necessary is that the ribs provide structural strength to support the plunger, and provide enough surface area in slideable contact with the plunger cavity walls to keep the plunger base 84 properly oriented in the plunger cavity 85.

Release button 16 carries a pin 108 under the button and attached to a deformable part of the button. Post 107, attached to handle 10 and spring 109, provides a forward force on a front interior wall of button 16 to bias the button forward. When the operator slides button 16 towards the rear of handle 10 to an operative position over detent 106, the button may be pushed down. As the button is pushed down, pin 108 pushes pin 94 out of detent 106. The plunger is then pushed forward by spring 28, and applies pressure to slide the implant out the end of the needle or cannula. As the needle is removed from the animal, the spring force on the plunger pushes the implant out of the needle. Forward motion of the plunger is stopped by face 112 of plunger base 84 abutting against conical wall 114 at the end of the plunger cavity 85 in handle 10. Wall 114 is conical in shape to guide the plunger 26 back into channel 116 and, subsequently, into cannula 14. This assists reinsertion of the plunger subassembly into the handle after removal of the subassembly for cleaning.

FIGS. 7A and 7B illustrate an alternative safety triqger design for the plunger release mechanism in FIG. 6. In FIGS. 7A and 7B, the release button 120 is designed to slide forward, i.e., in the direction of needle insertion, to an operative position. To prevent premature plunger release, safety ring 122 must be rotated on the injector handle 10 before button 120 will slide forward. The operator pushes on grooves 133 to rotate the ring until notch 124 is aligned with the slide groove for release button 120. Button 120 may then be pushed forward by the operator applying forward pressure to thumb pressure hump 126.

With button 120 in a forward position, pin 128, on the undersurface of the button, is aligned with pin 94 on the plunger base. Downward pressure on deformable button 120 at pressure bump 129 will push pin 128 down, and shove pin 94 out of detent 106 to thereby release the plunger. Spring 28 pushes the plunger 26 forward ejecting the implant from the cannula.

After release, the operator relaxes the downward pressure on button 120. Button 120 is pushed to the rear by spring 131 pushing between post 125, attached to the underside of the button, and post 127 attached to handle 10. The safety ring 122 is rotated back to the position shown in FIG. 7B by the operator so that notch 124 is n longer aligned with the slide groove for release button 120.

In FIGS. 8A and 8B, an alternative embodiment for the nose of the injector is shown. In this embodiment, the insertion depth for the cannula is adjusted by changing the length of nose 130 mounted on the front 132 of the injector handle. The nose would be a hollow tube with a knurl gripping surface 134 on the tube for twisting the tube into, and out of, cylindrical cavity 136 at the front 132 of the injector handle 10. There are no threads on the outside of tube 130 or the walls of cavity 136. There is merely a force-fit between tube 130 and cavity 136. Tube 130 should be made of a softer material than the front 132 of the injector to facilitate the force-fit between tube 130 and cavity 136.

The length of tube 130, relative to the length of the needle or cannula 138, controls the insertion depth of the needle. To change the insertion depth, the operator merely pulls the nose, or tube, 130 out of the injector, and inserts a tube of a different length. Of course, the operator could also change the needle length by interchanging needles, and thereby adjust the insertion depth.

While a number of preferred embodiments of the invention have been shown and described, it will be appreciated by one skilled in the art, that a number of further variations or modifications may be made without departing from the spirit and scope of our invention.

What is claimed is:

1. Implant injector for injecting an implant subcutaneously in an animal to a predetermined distance from the injection entry point into the animal, said injector comprising:
   a cannula for holding the implant and having a distal end;
   a handle for holding said cannula for subcataneous insertion into the animal;
   a nose means being adjustably mounted on the front of said handle and said cannula extending through said nose means, said nose means for stopping the subcutaneous insertion of said cannula at a predetermined insertion depth and being adjustably mounted in position on said handle relative to the distal end of the cannula to control the insertion depth;
   a plunger inside said handle and extending into said cannula and a spring for loading a force on the plunger for moving the plunger in said cannula;
   an operator controlled plunger release mechanism inside said handle for releasing said spring loaded plunger to move through said cannula and expel the implant after insertion of said cannula to the predetermined insertion depth;
   said plunger release mechanism having a detent for restraining said plunger against the spring load force on said plunger;
   a plunger release button in said release mechanism operated with a motion in the same direction as the insertion motion of said cannula into the animal for releasing said plunger from said detent; and
   a safety ring for enabling said plunger release button.

2. The injector of claim 1 and in addition:
   the front of said handle having exterior threads; and
   said nose means being a hollow tube with interior threads for engagement with the threads on said handle, said tube being threaded onto said handle and being adjustable relative to the handle and thus the cannula by rotation on the threads.

3. The injector of claim 1 and in addition:
   the front of said handle having a tubular cavity; and
   said nose means being interchangeable hollow tubes, each tube having an outer diameter to force fit in the tubular cavity at the front of said handle whereby hollow tubes of various lengths may be interchanged on the front of the handle to adjust the position of said nose means relative to the distal end of said cannula.

4. The injector of claim 1 and in addition:
   said cannula having a base for engagement with said handle and said handle having a front cavity for receiving the base of the cannula whereby cannula of different lengths and diameters may be interchanged on said handle.

5. Apparatus for injecting an implant subcataneously in an animal to a precise distance from an injection entry point in the skin of the animal, said apparatus comprising:
   needle means tubular shaped for carrying said implant inside said needle means as the needle means is inserted subcutaneously in the animal by an operator;
   means for holding said needle means;
   stop means on said holding means for stopping the subcutaneous insertion of said needle means at an insertion depth, said insertion depth being a precise distance from the entry point of said needle means into the animal;
   means for adjusting said stop means relative to the needle means to control the insertion depth; and
   means for expelling said implant out of said needle means after insertion of the needle means to the insertion depth, said expelling means has a length such that the end of said expelling means reaches the distal end of said needle means;
   said expelling means includes means for loading said expelling means against the implant with a load force at least sufficient to slide the implant out of said needle means when the needle is removed from the animal;
   release control means for restraining said expelling means against the load force from said loading means and for releasing said expelling means against the implant with said load force, said release control means having a safety release means for enabling said release control means, and said release control means operated with a motion in the same direction as the insertion motion of said needle means into the animal.

6. The apparatus of claim 5 and in addition:
   means for indicating the insertion depth.

7. The apparatus of claim 6 and in addition:
   said indicating means indicates a nominal insertion depth and adjustments from the nominal insertion depth when the depth is changed by said adjusting means.

8. The apparatus of claim 7 and in addition:
   means for engaging said needle means to, and disengaging said needle means from, said holding means; and
   said needle means having a cross-sectional width and length associated with the size of the animal being injected, said length having a precise positional relationship to the nominal insertion depth indicated by said indicating means.

9. The apparatus of claim 5 and in addition:

means for engaging said expelling means to, and disengaging said expelling means from, said holding means; and said expelling means having a length associated with the size of the animal being injected, said length having a precise positional relationship to the nominal insertion depth indicated by said indicating means.

10. The apparatus of claim 5 and in addition:

means for engaging said needle means to, and disengaging said needle means from, said holding means; and means for rotating to a plurality of predefined angular positions the engagement position of said needle means in said holding means.

* * * * *